(12) United States Patent
Asakawa et al.

(10) Patent No.: US 8,551,148 B2
(45) Date of Patent: Oct. 8, 2013

(54) LIGHT IRRADIATING APPARATUS AND LIGHT IRRADIATING METHOD

(75) Inventors: Takeshi Asakawa, Chiba (JP); Seija Wada, Kanagawa (JP); Yasufumi Shigeyoshi, Hyogo (JP)

(73) Assignee: Sony Corporation, Tokyo (JP)

( * ) Notice: Subject to any disclaimer, the term of this patent is extended or adjusted under 35 U.S.C. 154(b) by 219 days.

(21) Appl. No.: 13/069,926

(22) Filed: Mar. 23, 2011

(65) Prior Publication Data

US 2011/0245896 A1  Oct. 6, 2011

(30) Foreign Application Priority Data

Mar. 31, 2010  (JP) ................................. 2010-082362

(51) Int. Cl.
*A61N 5/06*  (2006.01)
(52) U.S. Cl.
USPC .................. 607/88; 607/89; 607/90; 607/91; 607/92; 607/93
(58) Field of Classification Search
USPC ........................................................ 607/88
See application file for complete search history.

(56) References Cited

U.S. PATENT DOCUMENTS

| 5,293,187 | A | * | 3/1994 | Knapp et al. | ................... 351/210 |
| 5,726,916 | A | * | 3/1998 | Smyth | ........................... 702/151 |
| 5,808,267 | A | * | 9/1998 | Eckhoff et al. | .......... 219/121.51 |
| 6,053,936 | A |   | 4/2000 | Koyama et al. | |
| 6,350,275 | B1 | * | 2/2002 | Vreman et al. | ................... 607/88 |
| 2010/0220291 | A1 | * | 9/2010 | Horning et al. | ............... 351/210 |

FOREIGN PATENT DOCUMENTS

| JP | 9-213101 | 8/1997 |
| JP | 2002-350790 | 12/2002 |

* cited by examiner

*Primary Examiner* — Sam Yao
*Assistant Examiner* — Boniface N Nganga
(74) *Attorney, Agent, or Firm* — K&L Gates LLP (57) ABSTRACT

Disclosed herein is a light irradiating apparatus including: a light source block configured to radiate a light to eyes of a user; a view line detection block configured to detect a view line direction of the user; and a light source control block configured to control the light radiated from the light source so as to restrict a light quantity in an area corresponding to a view line direction detected by the view line detection block.

9 Claims, 9 Drawing Sheets

FIG. 11

LIGHT IRRADIATING APPARATUS AND LIGHT IRRADIATING METHOD

CROSS REFERENCES TO RELATED APPLICATIONS

The present application claims priority to Japanese Priority Patent Application JP 2010-082362 filed in the Japan Patent Office on Mar. 31, 2010, the entire content of which is hereby incorporated by reference.

BACKGROUND

The present invention relates to a light irradiating apparatus and a light irradiating method and, more particularly, to a light irradiating apparatus and a light irradiating method that are for suitable use in helping recovery from a jetlag syndrome for example.

Usually, a travel by jetliner for example over regions having time differences of not shorter than four to five hours may cause a so-called jetlag, a temporary mental and/or physical disorder. This disorder often includes insomnia, drowsiness, fatigue, and/or anorexia.

Some people suffering from sleep disorder, depression, Alzheimer's disease, or the like are found having abnormal biorhythms, namely, a widely-defined jetlag. It is known that the symptoms of jetlag are improved by putting the biorhythm into order.

The period of the human biological clock is said to be around 25 hours, causing a difference of about one hour from the 24 hours in which the earth makes one rotation. This time lag may be reset by the exposition to the sunlight or other lights of high illumination, synchronizing the human biological clock with the earth's daily rotation.

Thus, the irradiation of high illumination puts the human biorhythm into order. Therefore, for a method of putting the human biorhythm into order, optical treatments are used in which a light irradiating apparatus for irradiating a light having as high an illumination as the sunlight irradiates the light to a client with a timing and a duration of irradiation in accordance with the degree of the client's biorhythm disorder.

With some light irradiating apparatuses used for optical treatment, the light irradiating block for irradiating light is fixed in front of the eyes of the wearer of a light irradiating apparatus with a head band (refer to Japanese Patent Laid-open No. Hei 9-213101) or the light source is arranged on the lens frame of the eye glass (refer to Japanese Patent Laid-open No. 2002-350790) in order to achieve small-sized apparatuses.

SUMMARY

It should be noted that, with the light irradiating apparatuses disclosed in the above-mentioned patent documents, the light irradiated from the light source is directly or indirectly projected uniformly onto the entire exposed portion of the eye of a wearer of a light irradiating apparatus.

Therefore, with these light irradiating apparatuses, a light of high luminance is radiated also in the direction of the view line within the sight of the wearer. The straight gaze of such a high-luminance light may fatigue or damage the eyes of the wearer.

Therefore, the present invention addresses the above-identified and other problems associated with related-art methods and apparatuses and solves the addressed problems by providing a light irradiating apparatus and a light irradiating method that are configured to improve the disorder in biorhythm while securing the safety of the eyes of the wearers of the light irradiating apparatus.

In carrying out the invention and according to one embodiment thereof, there is provided a light irradiating apparatus. This light irradiating apparatus has a light source block configured to radiate a light to eyes of a user; a view line detection block configured to detect a view line direction of the user; and a light source control block configured to control the light radiated from the light source so as to restrict a light quantity in an area corresponding to a view line direction detected by the view line detection block.

In carrying out the invention and according to another embodiment thereof, there is provided a light irradiating method. This light irradiating method has the steps of radiating a light to eyes of a user; detecting a view line direction of the user; and controlling a light source radiating a light to the eyes of the user so as to restrict a light quantity in an area corresponding to a view line direction detected in the view line detection step.

Consequently, the light quantity in the view line direction can be restricted while radiating lights of high luminance to the user's eyes. Thus, the load to the eyes can be reduced and the danger of damaging the health of the wearer can be mitigated while surely irradiating a light to put the biorhythm into order.

As described and according to the embodiments of the present invention, the light quantity in the view line direction can be restricted while radiating lights of high luminance to the user's eyes. Thus, the load to the eyes can be reduced and the danger of damaging the health of the wearer can be mitigated while surely irradiating a light to put the biorhythm into order. As a result, the light irradiating apparatus and the light irradiating method that are excellent in safety can be realized.

Additional features and advantages are described herein, and will be apparent from the following Detailed Description and the figures.

DETAILED DESCRIPTION

Embodiments of the present application will be described below in detail with reference to the drawings.

Figure 1A:
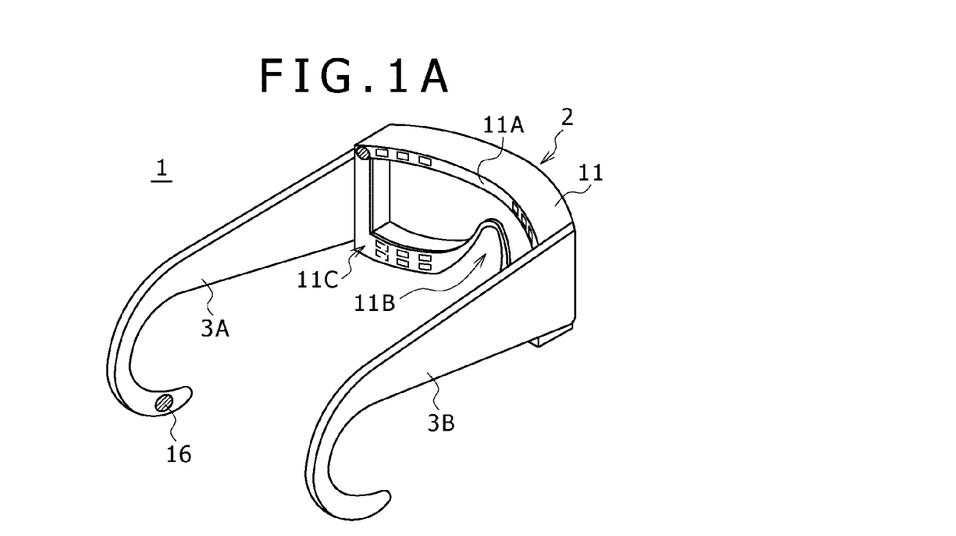
FIGS. 1A, 1B, and 1C are schematic diagrams illustrating an external configuration of a light irradiating apparatus practiced as one embodiment.
Figure 1B:
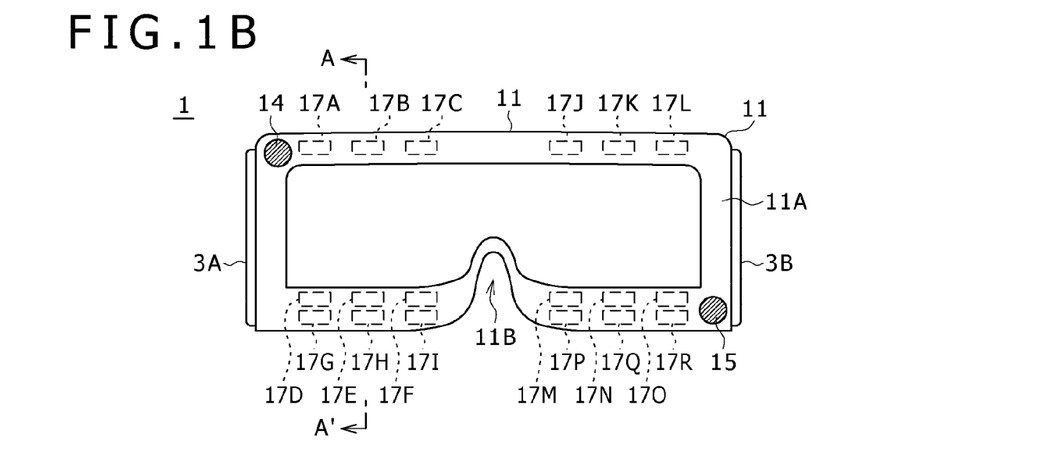

This present invention will be described in further detail by way of embodiments thereof with reference to the accompanying drawings. The description will be made in the following order:

(1) Embodiment
(2) Other embodiments (1) Embodiment (1-1) External Configuration of a Light Irradiating Apparatus Now, referring to FIG. 1, there is shown a light irradiating apparatus 1 of goggle type. As shown in FIG. 1A and FIG. 1B, the light irradiating apparatus 1 has a light irradiating section 2 and support sections 3A and 3B on both sides of the light irradiating section 2, for supporting the light irradiating section 2.

The support section 3A and the support section 3B are each linked at one end thereof with one end of the light irradiating section 2 and, at the other end, shaped into a bend along the base of the ear of a wearer of the light irradiating apparatus 1.

In the light irradiating section 2, a frame 11 is arranged. The frame 11 has a predetermined thickness to form a space therein and a size large enough for accommodate both eyes of the wearer. The frame 11 also has an abutting section 11A having a predetermined thickness that is opposed to the wearer when the light irradiating apparatus 1 is worn on the wearer, the cross section of the abutting section 11A being presenting approximately an "L" shape.

The frame 11 further has a catch section 11B that is bent at the center bottom thereof along the bend of the nose of the wearer. When the light irradiating apparatus 1 is worn, the catch section 11B positions the light irradiating apparatus 1 on the nose of the wearer such that the light irradiating section 2 comes in place.

Figure 1C:
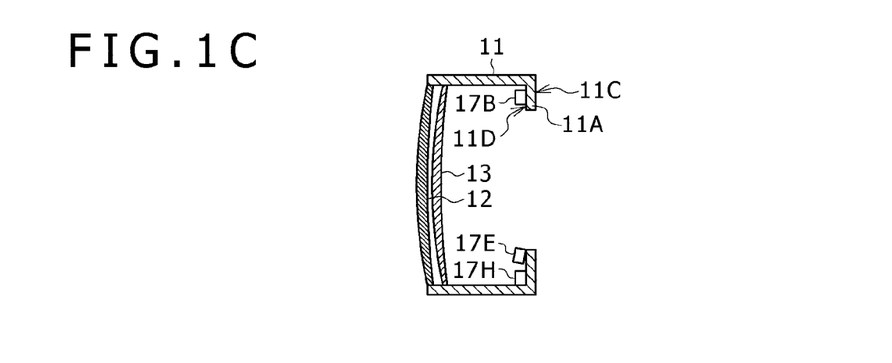

As shown in FIG. 1C, the light irradiating section 2 has a light reflecting plate 12 fits inside the frame 11 opposite to the abutting section 11A (namely, toward the front side).

The light irradiating section 2 also has a light diffusing plate 13 fits inside the frame 11 in approximately parallel to the light reflecting plate 12 to the side of the abutting section 11A (namely, toward the rear side) from the light reflecting plate 12. The light diffusing plate 12 diffuses an incoming light into a uniform light.

An electrode 14 is installed in the upper left corner of a surface (hereafter referred to as an abutting surface) 11C abutting the face of the wearer in the abutting section 11A of the frame 11. Likewise, in the lower right corner, an electrode 15 is installed. The electrode 14 and the electrode 15 are each made of a metal conductor for example, the electrode 14 being abutted to the upper left section (approximately on the outside end of the left eyebrow) of the left eye of the wearer and the electrode 15 being abutted to the lower right section (approximately the outer corner of the right eye) of the right eye of the wearer when the light irradiating apparatus 1 is worn.

A reference electrode 16 made of a metal conductor is installed on the other end of the support section 3A at a position on the surface of abutting the base of the ear when the light irradiating apparatus 1 is worn. When the light irradiating apparatus 1 is worn, the reference electrode 16 abuts the base of the ear of the wearer.

A total of nine LEDs (Light Emitting Diodes) 17A through 17I and 17J through 17R are installed on the surface (hereafter also referred to as light source arranged surface) opposite to the abutting surface 11C in the abutting section 11A of the frame 11, the LEDs 17A through 17I being arranged on the left side and the LEDs 17J through 17R on the right side.

To be more specific, the LEDs 17A through 17C are arranged in the upper left of the light source arranged surface 11D. The LEDs 17D through 17F and 17G through 17I are arranged on the lower left of the light source arranged surface 11D in two upper and lower rows.

Figure 2A:
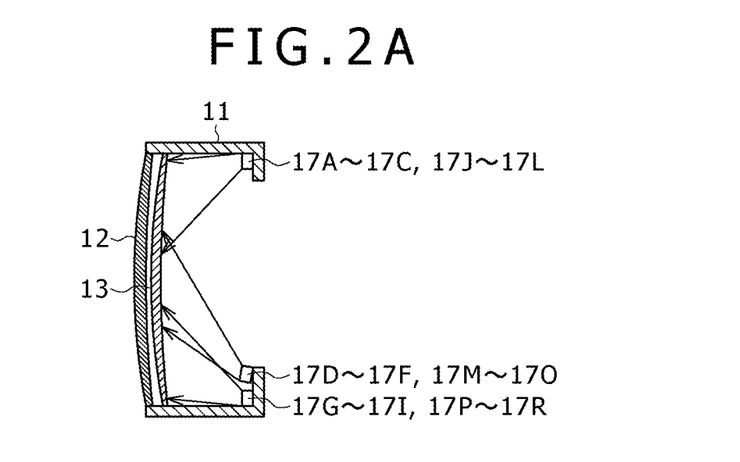
FIGS. 2A and 2B are schematic diagrams illustrating LED irradiating areas.
Figure 2B:
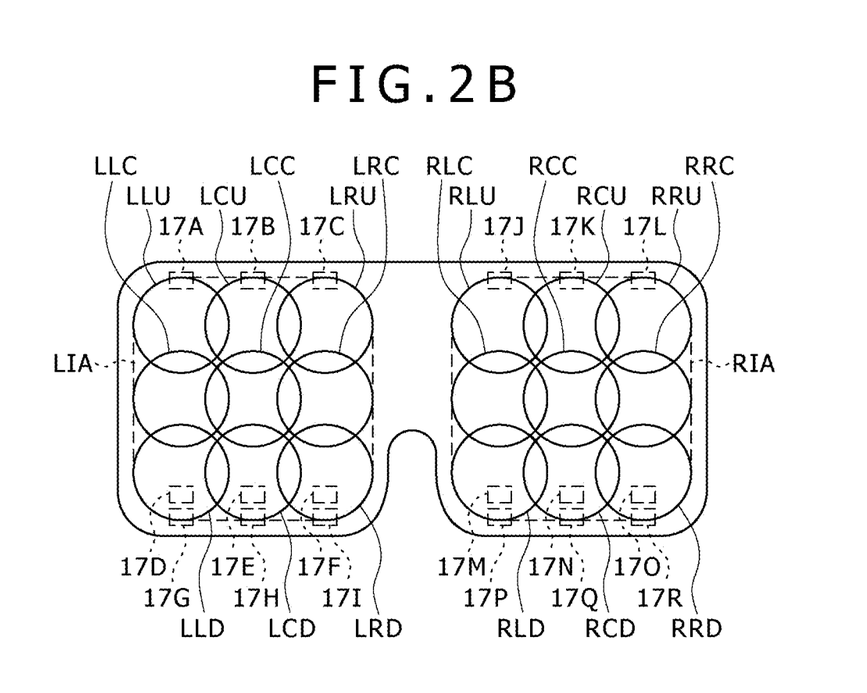

As shown in FIGS. 2A and 2B, the LEDs 17A through 17C irradiate an upper left area LLU, an upper center area LCU, and an upper right area LRU in an area LIA (hereafter also referred to as a left irradiation area) of a predetermined range in the left half in the light diffusing plate 13.

The LEDs 17D through 17F irradiate a center left area LLC, a front face (center) area LCC, and a center right area LRC in the left irradiation area LIA. The LEDs 17G through 17I irradiate a lower left area LLD, a lower center area LCD, and a lower right area LRD in the left irradiation area LIA.

The LEDs 17A through 17I irradiate the light diffusing plate 13 such that areas LLU, LCU, LRU, LLC, LCC, LRC, LLD, LCD, and LRD each provide an area equivalent to about ⅑ of the left irradiation area LIA. Therefore, the left irradiation area LIA provides an area in which the lights outputted from LEDs 17A through 17I are diffused by the light diffusing plate 13 to be irradiated into the left eye of the wearer.

On the other hand, the LEDs 17J through 17L are arranged in the upper right side of the light source arranged surface 11B. LEDs 17M through 17O and LEDs 17P through 17R are arranged in the lower right side in the light source arranged surface 11D in two upper and lower rows.

The LEDs 17J through 17L irradiate upper left area RLU, upper center area RCU, and upper right area RRU in a area (hereafter also referred to a right irradiation area) RIA of a predetermined range of the right half in the light diffusing plate 13.

The LEDs 17M through 17O irradiate center left area RLC, front face area RCC, and center right RRC in the right irradiation area RIA. The LEDs 17P through 17R irradiate lower left area RLD, lower center area RCD, and lower right area RRD in the right irradiation area RIA.

The LEDs 17J through 17R irradiate the light diffusing plate 13 such that areas RLU, RCU, RRU, RLC, RCC, RRC, RLD, RCD, and RRD each provide an area equivalent to about ⅑ of the right irradiation area RIA. Therefore, the right irradiation area RIA provides an area in which the lights outputted from LEDs 17J through 17R are diffused by the light diffusing plate 13 to be irradiated into the right eye of the wearer.

It should be noted that the light irradiation area LIA and the right irradiation area RIA are generically referred to as irradiation area IA unless otherwise specified. Area LLU and area RLU are generically referred to as area LU unless otherwise specified. Likewise, area LCU and area RCU, area LRU and area RRU, area LLC and area RLC, area LCC and area RCC, area LRC and area RRC, are LLD and area RLD, area LCD and are RCD, and area LRD and area RRD are generically referred to as area CU, area RU, area LC, area CC, area RC, area LD, area CD, and area RD, respectively, unless otherwise specified.

Figure 3:
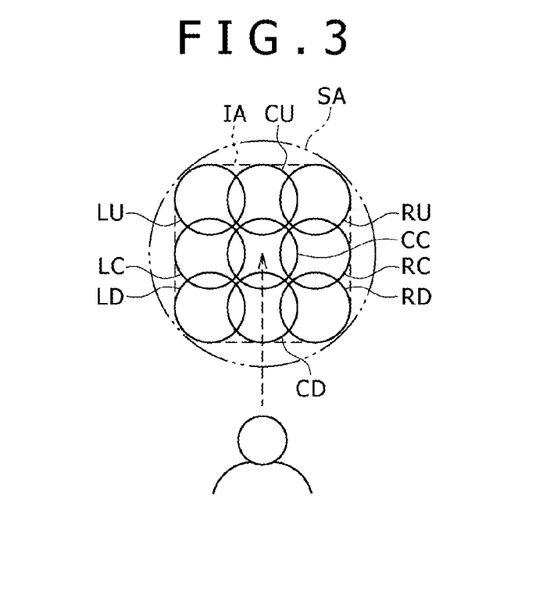
FIG. 3 is a schematic diagram illustrating irradiating areas for the entire field of view.

As shown in FIG. 3, the light irradiating apparatus 1 is configured to radiate lights from the LEDs 17A through 17R to the irradiation area IA in which the overall sight SA of the wearer of the light irradiating apparatus 1 is almost covered.

Figure 4:
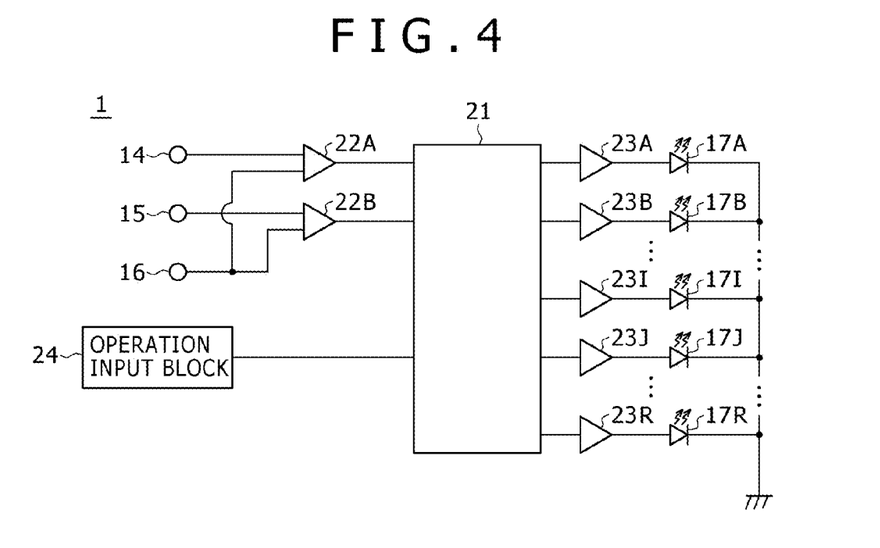
FIG. 4 is a circuit diagram illustrating an exemplary circuit configuration of the light irradiating apparatus.

It should be noted that the LEDs 17A through 17R are configured to radiate lights by the power supplied from a power supply block, not shown, under the control of a microcontroller 21 (refer to FIG. 4).

It should be noted that the LEDs 17A through 17R can output lights of illumination high enough for the light diffused by the light diffusing plate 13 to be radiated onto the eyes of the wearer to put the biorhythm of the wearer into order.

In addition, the light irradiating section 2 has, at a predetermined position thereof, an operator input block 24 (refer to FIG. 4) having controls through which the user enters operation signals.

(1-2) Exemplary Circuit Configuration of the Light Irradiating Apparatus

The following describes an exemplary circuit configuration of the light irradiating apparatus 1. As shown in FIG. 4, the light irradiating apparatus 1 is configured that each component block operates on the power supplied from the power supply block, the microcontroller 21 collectively controlling all the component blocks. It should be noted that the microcontroller 21 and the power supply block are arranged inside the light irradiating apparatus 1.

The microcontroller 21 is based on a CPU (Central Processing Unit), a ROM (Read Only Memory), a RAM (Random Access Memory) providing the work memory of the CPU, a timer, an arithmetic unit, and so on.

An amplifier 22A amplifies a potential difference between the electrode 14 and the reference electrode 16 as a left potential difference, supplying the potential difference to the microcontroller 21. An amplifier 22B amplifies a potential difference between the electrode 15 and the reference electrode 16 as a right potential difference, supplying the right potential difference to the microcontroller 21.

In response to an operation input executed through the controls of the operator input block 24, the operator input block 24 gives data (hereafter referred to as irradiation time data) representative of a light irradiation start time and a light irradiation end time to the microcontroller 21.

The microcontroller 21 supplies control signals to the LEDs 17A through 17R via amplifiers 23A through 23R in order to illuminate the LEDs 17A through 17R with predetermined light quantities on the basis of the obtained left and right potential differences. Details of this processing will be described later.

Figure 5:
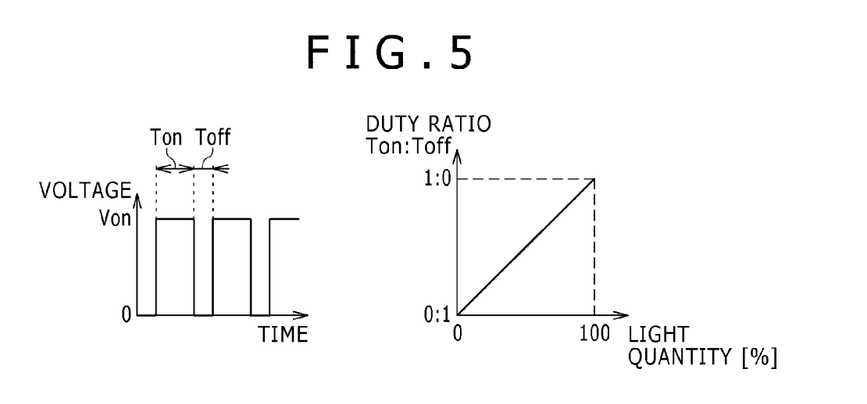
FIG. 5 shows graphs indicative of LED light quantity control.

As shown in FIG. 5, if a pulse signal having a frequency of several tens KHz or higher for example is supplied, the quantity of light of each of the LEDs 17A through 17R is determined in accordance with the ratio between time Ton in which a voltage in one period is supplied and time Toff in which no voltage is supplied.

Consequently, the microcontroller 21 supplies a control signal based on a pulse signal having a frequency of several tens KHz or higher to the LEDs 17A through 17R, thereby controlling the quantity of light that is illuminated from each of the LEDs 17A through 17R.

(1-3) Light Irradiation Processing

With the microcontroller 21, a program (hereafter referred to as a light irradiation program) for controlling the quantity of light outputted from the LEDs 17A through 17R is stored in the ROM. If instructed for the execution of the light irradiation program, the microcontroller 21 lords the light irradiation program from the ROM into the RAM to executed the specified light irradiation processing.

Figure 6:
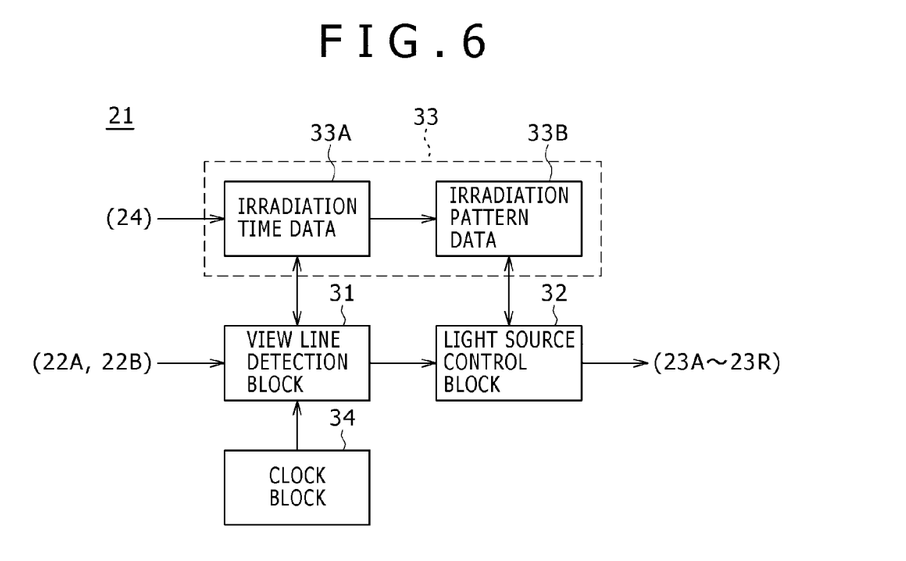
FIG. 6 is a block diagram illustrating an exemplary functional configuration of a microcontroller.

As shown in FIG. 6, in executing the light irradiation processing, the microcontroller 21 functions as a view line detection block 31, a light source control block 32, a storage block 33, and a clock block 34.

The view line detection block 31 reads irradiation time data 33A entered via the operator input block 24 and stored in the storage block 33. From the time when the time supplied from the clock block 34 at predetermined intervals reaches the irradiation start time indicated in the irradiation time data 33A, the view line detection block 31 gets the left potential difference and the right potential difference from the amplifier 22A and the amplifier 22B, respectively, at predetermined intervals (several tens KHz for example), thereby detecting the view line of the wearer.

Figure 7:
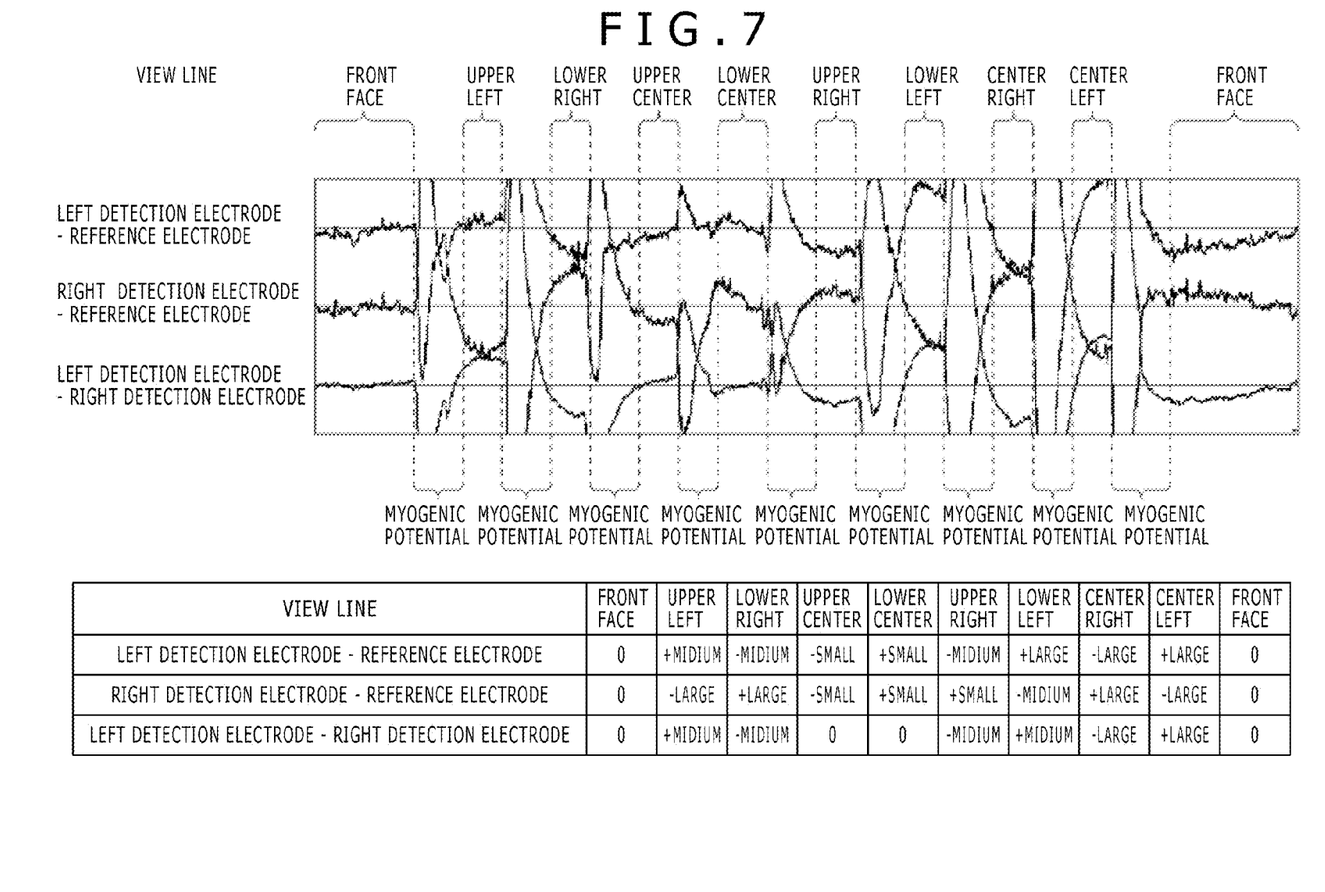
FIG. 7 shows charts indicative of changes in potential difference depending on the directions of view line.

FIG. 7 shows experiment results obtained by measuring the potential differences between the electrodes and the reference electrode and the potential differences between the electrodes with the reference electrode arranged on the left ear lobule and the electrodes arranged in the upper left of the left eye and the lower right of the right eye, in the state of which the view line is moved in various directions. In FIG. 7, the electrode arranged in the upper left of the left eye is referred to also as a left detection electrode and the electrode arranged in the lower right is referred to also as a right detection electrode.

In this measurement, the view line is moved from front face to upper left, lower right, upper center, lower center, upper right, lower left, center right, center left, and front face in this sequence, stopping the view line at each position for a predetermined period of time. At this time, as shown in FIG. 7, while the view line is in a stopped state in each direction, the potential difference between the left detection electrode and the reference electrode, the potential difference between the right detection electrode and the reference electrode, and the potential difference between the left detection electrode and the right detection electrode are different from each other in sign and magnitude depending on the direction in which the view line is stopped.

To be more specific, measuring at least the potential difference between the left detection electrode and the reference electrode and the potential difference between the right detection electrode and the reference electrode allows the detection of view line directions on the basis of the sign and magnitude of each potential difference.

It should be noted that a big change of each potential in moving the view line in FIG. 7 is indicative that the myogenic potential at the time the view line is moved is measured. The myogenic potential is about 1000 times as large as the ocular potential, so that the myogenic potential and the ocular potential can easily be distinguished from each other.

Therefore, the view line detection block 31 obtains the left potential and the right potential from the amplifier 22A and the amplifier 22B, respectively, at predetermined intervals. If the left potential and the right potential are found to be equal to or above the threshold that is the myogenic potential, it is determined that the myogenic potential is being measured and view line is moving.

If the left potential and the right potential are found to be below the threshold, the view line detection block 31 determines whether the left potential and the right potential are any one of three steps "large," "medium," and "small" that are set for the detection of nine types view lines for example. The nine directions are "front face," "upper center," "lower center," "center right," "center left," "upper right," "lower right," "upper left," and "lower left."

Next, the view line detection block 31 compares the signs and magnitudes of the left potential and the right potential with the table indicative of the signs and magnitudes in the nine view line directions shown in FIG. 7, thereby detecting the view line of the wearer.

Every time the data (hereafter referred to also as view line data) indicative of the detected view line directions or that the view line is moving is detected, the view line detection block 31 transmits the detected view line data to the light source control block 32.

Obtaining the view line data, the light source control block 32 reads the data (hereafter referred to also as irradiation pattern data) 33B indicative of the irradiation patterns corresponding to the view line directions indicated by the view line data from the storage block 33.

Figure 8A:
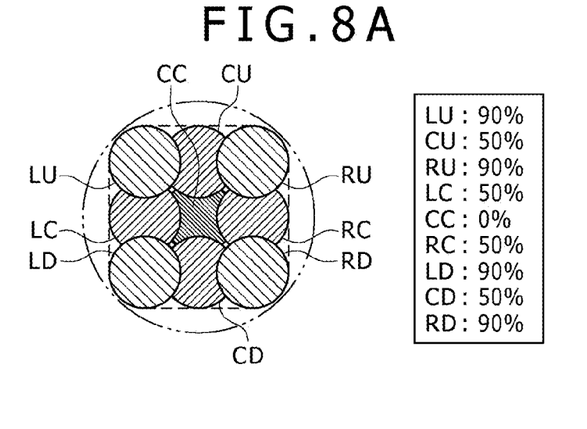
FIGS. 8A, 8B, and 8C are schematic diagrams illustrating the ratios of light quantity to the directions of view line.

The storage block 33 stores the irradiation patterns corresponding to the nine types of view line directions. To be more specific, with the irradiation pattern with the view line direction being "front face," the quantity of light radiated to center CC=0%, the quantity of light radiated to upper center CU, lower center CD, center left LC, and center right RC adjacent to the up and down and the left and right of center CC=50%, and the quantity of light radiated to upper left LU, upper right RU, lower left LD, and lower right RD obliquely adjacent to center CC=90% as shown in FIG. 8A.

Figure 8B:
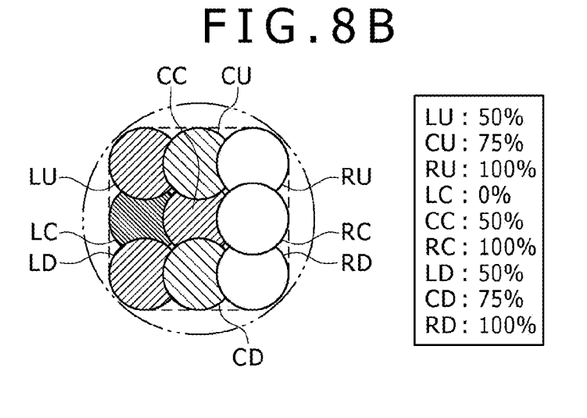

With the irradiation pattern with the view line direction being "center left," the quantity of light radiated to center left LC=0%, the quantity of light radiated to upper left LU, lower left LD, and center CC adjacent to the up and down and the right of center left LC=50%, the quantity of light radiated to upper center CU and lower center CD obliquely adjacent to center left LC=75%, and the quantity of light radiated to other upper right RU, center right RC, and lower right RD=100% as shown in FIG. 8B.

Figure 8C:
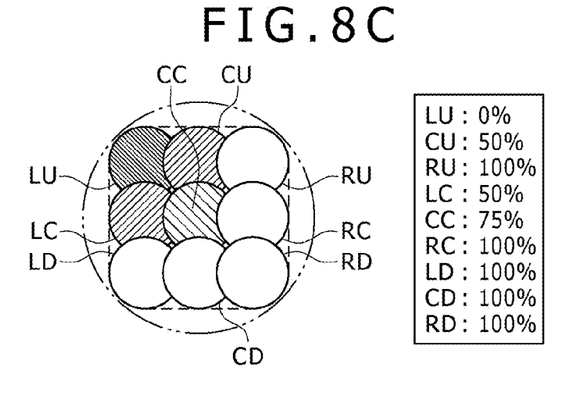

Further, with the irradiation pattern with the view line direction being "upper left," the quantity of light radiated to upper left LU=0%, the quantity of light radiated to upper center CU and center left LC adjacent to the right and lower of upper left LU=50%, the quantity of light radiated to center CC obliquely adjacent to upper left LU=75%, and the quantity of light radiated to other upper right RU, center right RC, lower right RD, lower center CD, and lower left=100% as shown in FIG. 8C.

With the irradiation patterns with the view line directions being "upper center," "lower center," and "center right," the quantity of light radiated to the area in the direction of the view line=0%, the quantity of light radiated to the areas adjacent to the up and down and left and right of the area in the view line direction=50%, the quantity of light radiated to the areas obliquely adjacent to the area of view line direction=75%, and the quantity of light radiated to other areas=100% like the patterns in the case where the view line direction is "center left."

With the irradiation patterns with the view line directions being "lower left," "upper right," and "lower right," the quantity of light radiated to the area in the direction of the view line=0%, the quantity of light radiated to the areas adjacent to the up and down and left and right of the area in the view line direction=50%, the quantity of light radiated to the areas obliquely adjacent to the area of view line direction=75%, and the quantity of light radiated to other areas=100% like the patterns in the case where the view line direction is "upper left."

Reading the irradiation pattern data 33B corresponding to the view line direction indicated by the view line data from the storage block 33, the light source control block 32 transmits control signals for outputting the lights from the LEDs 17A through 17R with the light quantities corresponding to the irradiation patterns thus read to the amplifiers 23A through 23R.

If the view line data indicative that the view line is moving is supplied from the view line detection block 31, then the light source control block 32 transmits the control signal for controlling the light quantity to 0% to the amplifiers 23A through 23R to prevent the all LEDs 17A through 17R from outputting light.

Consequently, the light irradiating apparatus 1 can control the quantity of the light to be radiated to the areas corresponding to the view line of the wearer so as to radiate, to the eyes of the wearer, the light that increases in quantity as the light gets farther from the area corresponding to the view line.

During a period of time from irradiation start to irradiation end, the view line detection block 31 and light source control block 32 repeat the view line detection and the irradiation control described above, thereby outputting, from the LEDs 17A through 17R, the lights with the light quantities varied in accordance with the wearer's view line directions.

(1-4) Light Irradiation Processing Procedure

Figure 9:
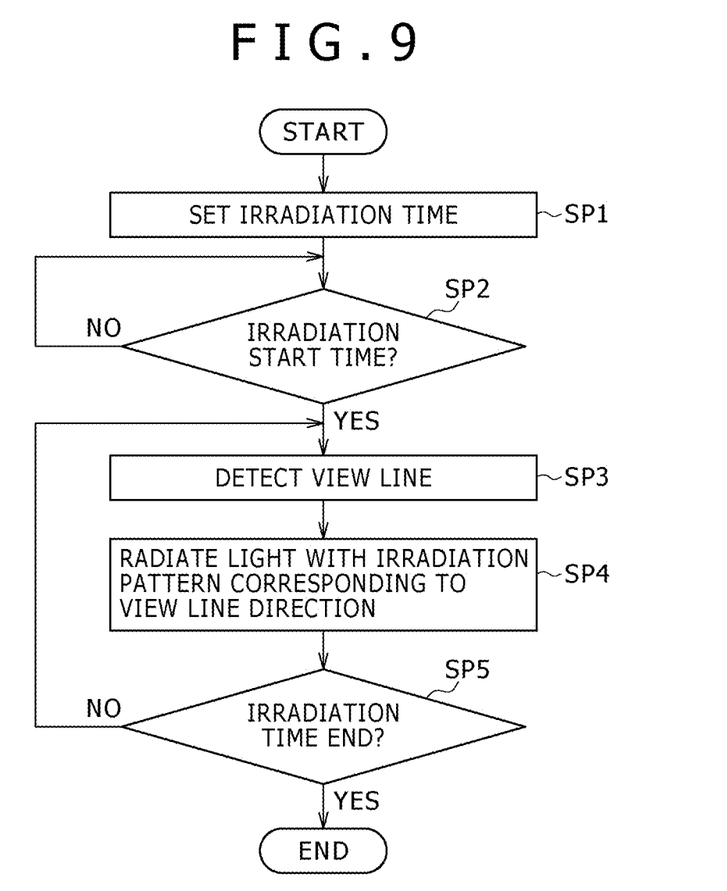
FIG. 9 is a flowchart indicative of a light irradiation processing procedure.

The following describes the procedure of the light irradiation processing described above with reference to the flowchart shown in FIG. 9. The microcontroller 21 enters the start step of routine RT1 and moves to step SP1 to obtain an irradiation start time and an irradiation end time through the operator input block 24 and store the obtained times in the storage block 33 as irradiation time data, moving to step SP2.

In step SP2, the microcontroller 21 reads the irradiation time data from the storage block 33 to determine whether the irradiation start time indicated in the irradiation time data has been reached or not. Until the irradiation start time is reached, the microcontroller 21 repeats this step SP2.

If the decision in step SP2 is in the affirmative, namely, the irradiation start time is found reached, then the microcontroller 21 goes to step SP3 to obtain a left potential difference between the electrode 14 and the reference electrode 16 and a right potential difference between the electrode 15 and the reference electrode 16.

Next, the microcontroller 21 detects the view line direction of the wearer on the basis of the left potential difference and the right potential difference and goes to step SP4. In step SP4, the microcontroller 21 reads the irradiation pattern corresponding to the detected view line direction from the storage block 33 and outputs the lights having light quantities corresponding to the irradiation pattern from the LEDs 17A through 17R, moving to step SP5.

In step SP5, the microcontroller 21 determines whether the irradiation end time indicated in the irradiation time data has been reached or not. If the decision is in the negative, then the microcontroller 21 returns to step SP3 to repeat steps SP3 through SP5 until the affirmative decision is obtained.

If the decision in step SP5 is found to be in the affirmative, then the microcontroller 21 moves to the next step to end the processing.

(1-5) Operation and Effects

In the configuration described so far, the light irradiating apparatus 1 has the electrode 14 and the electrode 15 arranged at the upper left of the left eye and the lower right of the right eye that are positions different in the up and down and left and right directions about the eyes of the wearer and the reference electrode 16 arranged at the base of the ear of the wearer. In addition, the light irradiating apparatus 1 has the LEDs 17A through 17R that radiate lights to the almost the overall sight SA of the wearer.

Next, the light irradiating apparatus 1 detects the view line direction of the wearer on the basis of the left potential difference between the electrode 14 and the reference electrode 16 and the right potential difference between the electrode 15 and the reference electrode 16 to control the light quantities of the lights to be outputted from the LEDs 17A through 17R so that the light quantities in the view line direction are restricted.

Consequently, the light irradiating apparatus 1 can restrict the light quantities in the view line direction while radiating the lights of high luminance to the user's eyes, thereby radiating the lights of high luminance to the retina of the eyes of the wearer except for the yellow spots called macula that are higher in resolution than the other parts of the retina.

Therefore, while radiating the lights strong enough for putting the biorhythm into order to the eyes of the wearer of the light irradiating apparatus 1, the light irradiating apparatus 1 can reduce the load to the eyes and mitigate the danger of damaging the health of the wearer.

In addition, the light irradiating apparatus 1 has a plurality of light sources LEDs 17A through 17I and LEDs 17J through 17R that irradiate small areas obtained by dividing the sights of the left eye and the right eye.

Consequently, the light irradiating apparatus 1 can control the light quantities finely in accordance with view line directions to surely restrict the radiated light quantity for the macula that are higher in resolution, radiating the lights of high luminance to the areas other than the macula with a simple configuration.

Further, if the left potential difference between the electrode 14 and the reference electrode 16 and the right potential difference between the electrode 15 and the reference electrode 16 are equal to or above a predetermined threshold, the light irradiating apparatus 1 determines that a myogenic potential is being measure, or the view line is moving, thereby preventing the LEDs 17A through 17R from outputting lights.

Consequently, the light irradiating apparatus 1 can surely prevent the radiation of lights of high luminance in the view line direction while the wearer is moving the view line, thereby further enhancing the safety in irradiation.

According to the configuration described above, the electrode 14 and the electrode 15 for detecting the view line direction of the wearer and the LEDs 17A through 17R for radiating lights to the sight of the wearer are arranged to detect the view line direction of the wearer from the potential difference between the electrodes 14 and 15 and the reference electrode 16, thereby restricting the light quantity to be projected to the areas corresponding to the view line directions of the wearer.

Consequently, the light irradiating apparatus 1 can restrict the light quantity in the view line direction while radiating lights of high luminance to the user's eyes, thereby reducing the load to the eyes and mitigating the danger of damaging the health of the wearer.

(2) Other Embodiments of the Invention

In the embodiment described above, the LEDs 17A through 17I and the LEDs 17J through 17R are arranged on the light source arranged surface 11D of the light irradiating section 2. The lights outputted from the LEDs 17A through 17R are diffused by the light diffusing plate 13 to be projected to the eyes of the wearer of the light irradiating apparatus 1. However, the embodiments of the present invention are not limited to this configuration.

Figure 10:
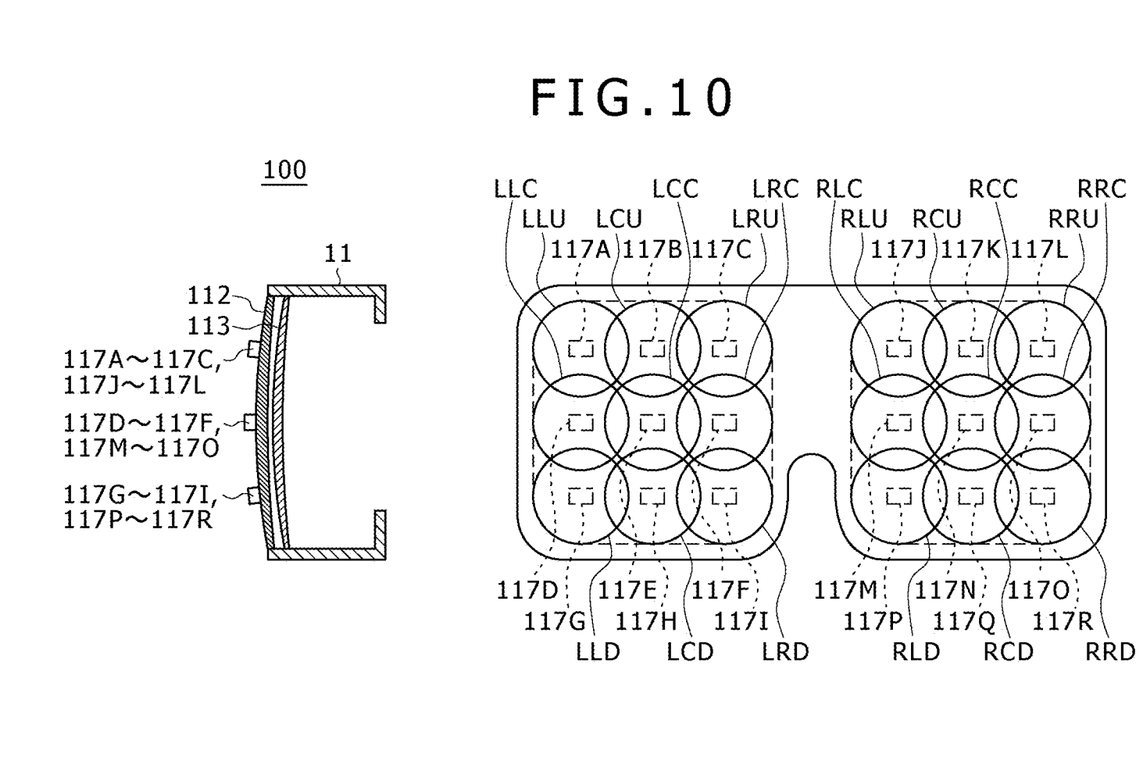
FIG. 10 is a schematic diagram illustrating a light irradiating apparatus practiced as another embodiment.

For example, as shown in FIG. 10, with reference to which the components similar to those previously described with reference to FIG. 1 are denoted by the same reference numerals, a light irradiating apparatus 100 has a transparent plate 112 and a light diffusing plate 113 at the same positions as those of the light reflecting plate 12 and the light diffusing plate 13.

In addition, the light irradiating apparatus 100 has nine LEDs 117A through 117I and LEDs 117J through 117R on the left and right sides, respectively, on the opposite side of the light diffusing plate 113 in the transparent plate 112.

Like the LEDs 17A through 17I of the light irradiating apparatus 1, the LEDs 117A through 117I radiate lights to areas LLU, LCU, LRU, LLC, LCC, LRC, LLD, LCD, and LRD in the light diffusing plate 113.

Also, like the LEDs 17J through 17R of the light irradiating apparatus 1, the LEDs 117J through 117R radiate lights to areas RLU, RCU, RRU, RLC, RCC, RRC, RLD, RCD, and RRD in the light diffusing plate 113.

As described above, the light irradiating apparatus 100 is configured such that the lights outputted from the LEDs 117A through 117R are diffused by the light diffusing plate 113 to be radiated to the eyes of the wearer of the light irradiating apparatus 100.

Figure 11:
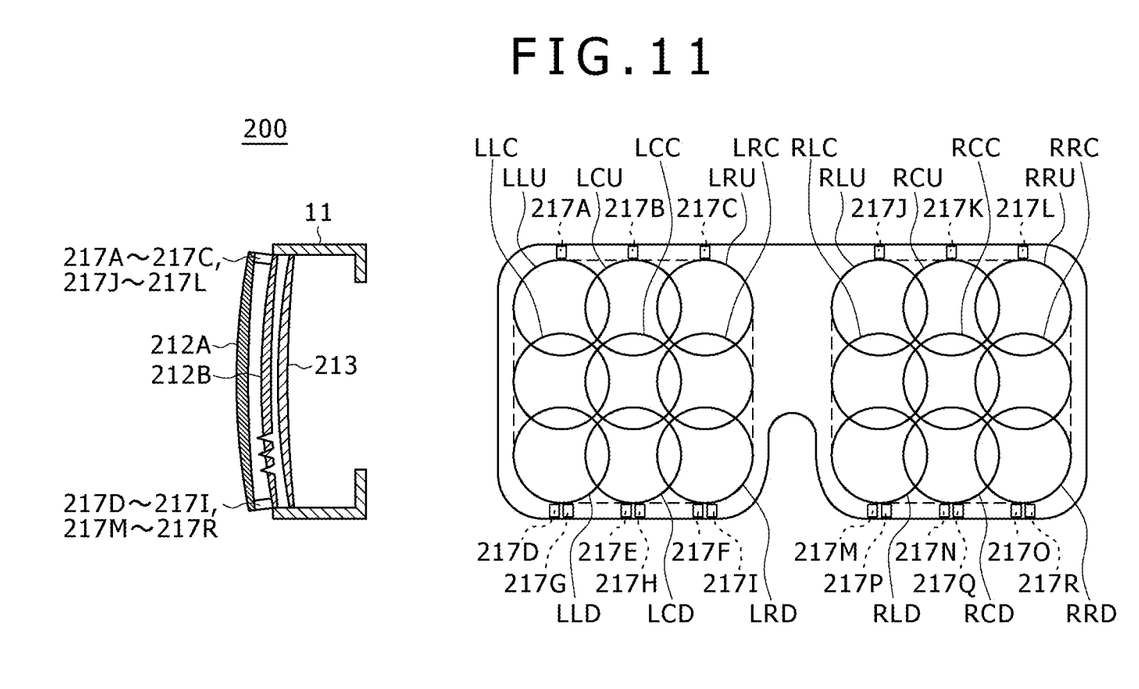
FIG. 11 is a schematic diagram illustrating a light irradiating apparatus practiced still another embodiment.

In an another example, as shown in FIG. 11, with reference to which the components similar to those previously described with reference to FIG. 1 are denoted by the same reference numerals, a light irradiating apparatus 200 has a high refraction index material 212A, a low refraction index material 212B, and a light diffusing plate 213 instead of the light reflecting plate 12 and the light diffusing plate 13 of the light irradiating apparatus 1 shown in FIG. 1.

A space between the high refraction index material 212A and the low refraction index material 212B functions as a waveguide in which lights go reflecting from both the materials. The low refraction index material 212B has many minute scratches. The light arriving at the scratches on the low refraction index material 212B is guided from the scratches to the light diffusing plate 213.

The light irradiating apparatus 200 has LEDs 217A through 217C and LEDs 217J through 217L in the upper left and the upper right, respectively, between the high refraction index material 212A and the low refraction index material 212B. The light irradiating apparatus 200 also has LEDs 217D through 217I and LEDs 217M through 217R in the lower left and the lower right, respectively, between the high refraction index material 212A and the low refraction index material 212B.

Like the LEDs 17A through 17I of the light irradiating apparatus 1, the LEDs 217A through 217I radiate lights to areas LLU, LCU, LRU, LLC, LCC, LRC, LLD, LCD, and LRD in the light diffusing plate 213.

Like the LEDs 17J through 17R of the light irradiating apparatus 1, the LEDs 217J through 217R radiate lights to areas RLU, RCU, RRU, RLC, RCC, RRC, RLD, RCD, and RRD in the light diffusing plate 213.

As described above, the light irradiating apparatus 200 is configured such that the lights outputted from the LEDs 217A through 217R are diffused by the light diffusing plate 213 via the waveguide formed between the high refraction index material 212A and the low refraction index material 212B to be radiated to the eyes of the wearer of the light irradiating apparatus 200.

In the embodiments described above, the irradiation area IA are divided into nine small areas LU, CU, RU, LC, CC, RC, LD, CD, and RD. The LEDs 17A through 17I and LEDs 17J through 17R are arranged for radiating lights to these nine small areas.

However, the embodiments of the present invention are not restricted to this configuration. For example, the number of small areas obtained by dividing the irradiation area IA may be other than nine and the number of light sources that irradiate the small areas may be any other than those described above. Namely, the irradiation area IA may be divided smaller with the number of corresponding light sources increased accordingly to control the light quantity in the view line direction of the wearer more finely.

In the embodiments described above, the view line direction can be detected in any one of the nine directions. However, the embodiments of the present invention are not restricted to this configuration. The number of directions may be other than nine if the view line direction can be detected.

In the embodiments described above, the view line is detected by comparing the sign and magnitude of the left potential difference and the right potential difference with a table listing the sign and magnitude in the nine view line directions. The embodiments of the present invention are not restricted to this configuration. For example, any other methods may be used for detecting the view line direction if the view line direction can be detected from the sign and magnitude of the left potential difference and the right potential difference.

In the embodiments described above, the electrode 14 and the electrode 15 are arranged in the upper left and the lower right of the abutting section 11A such that the electrode 14 and the electrode 15 abut the upper left of the left eye and the lower right of the right eye of the wearer, respectively.

However, the embodiments of the present invention are not restricted to this configuration. For example, the electrode 14 and the electrode 15 may be arranged any other positions if the electrode 14 and the electrode 15 can be arranged at positions where the up and down directions and the left and right directions are different so as to be able to detect the view line in the up and down directions and the left and right directions.

In the embodiments described above, the irradiation start time and the irradiation end time are entered through the operator input block 24. However, the embodiments of the present invention are not restricted to this configuration. For example, if the embodiments are used aboard a jetliner, the irradiation start time and the irradiation end time set to cope with the jetlag in match with the destination's local time may be entered in the light irradiating apparatus 1 from the jetliner via a predetermined communication section.

Further, in the embodiments described above, the microcontroller 21 executes the above-mentioned irradiation processing in accordance with a program stored in the ROM. However, the embodiments of the present invention are not restricted to this configuration. For example, the microcontroller 21 may execute the irradiation processing in accordance with a program that is installed in the microcontroller 21 from a storage media or downloaded from the Internet. Alternatively, the microcontroller 21 may execute the irradiation processing in accordance with a program installed in the microcontroller 21 via any other routes.

Moreover, in the embodiments described above, the LEDs 17A through 17R are arranged as the light source block, the view line detection block 31 is arranged as the view line detection block, and the light source control block 32 is arranged as the light source control block. However, the embodiments of the present invention are not restricted to this configuration. For example, light sources, a view line detection block, and a light source control block that are based on any other configurations may be arranged.

As described above, the embodiments of the present invention are applicable to optical treatments for mitigating jetlag syndromes for example.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A light irradiating apparatus comprising:
a frame;
a reflecting plate attached to the frame;
a light source block formed on peripheral edges of the frame and configured and arranged to radiate a light to eyes of a user by radiating the light from the light source block to the reflecting plate, and then reflecting the light off the reflecting plate back to the eyes of the user;
a view line detection block configured to detect a view line direction of the user, the view line detection block including two electrodes, and a reference electrode, said view line detection block detecting a view line direction of said user from a potential difference between said two electrodes and said reference electrode; and
a light source control block configured to control the light radiated from said light source so as to restrict a light quantity in an area corresponding to the view line direction detected by said view line detection block.

2. The light irradiating apparatus according to claim 1, wherein said view line detection block detects a movement of the view line of said user by comparing said potential difference with a threshold at which the view line of said user is assumed moving, and
said light source control block controls said light source block not to radiate a light if the movement of the view line of said user is detected by said view line detection block.

3. The light irradiating apparatus according to claim 1, wherein said electrodes are arranged at positions different in up and down direction and left and right direction around the eyes of said user.

4. The light irradiating apparatus according to claim 1, wherein said light source block is composed of a plurality of light sources each configured to radiate a light to one of small areas of the reflecting plate, said small areas obtained by dividing an area that is a range of sight of said user.

5. A light irradiating method comprising the steps of:
radiating a light to eyes of a user, the light being radiated from a light source block formed on peripheral edges of a frame of a light irradiating apparatus to a reflecting plate and back to the eyes of a user;
detecting a view line direction of the user based on a potential difference between two electrodes provided on the frame and a reference electrode; and
controlling a light source radiating a light to the eyes of the user so as to restrict a light quantity in an area corresponding to a view line direction detected in said view line detection step.

6. A light irradiating apparatus comprising:
a frame;
a reflecting plate attached to the frame;
light source means formed on peripheral edges of the frame and configured and arranged for radiating a light to eyes of a user by radiating the light from the light source means to the reflecting plate, and then reflecting the light off the reflecting plate back to the eyes of the user;
view line detection means for detecting a view line direction of the user, the view line detection block including two electrodes formed on the second surface, and a reference electrode, said view line detection block detecting a view line direction of said user from a potential difference between said two electrodes and said reference electrode; and
light source control means for controlling the light radiated from said light source so as to restrict a light quantity in an area corresponding to—a the view line direction detected by said view line detection means.

7. The light irradiating apparatus according to claim 1, wherein the frame includes an abutting section, the abutting section having a first surface and a second surface opposed thereto, wherein the light source block is formed on the first surface of the abutting section.

8. The light irradiating apparatus according to claim 7, wherein the two electrodes are formed on the second surface of the abutting section.

9. The light irradiating apparatus according to claim 1, further comprising a light diffusing plate formed between the light source block and the light reflecting plate.

* * * * *

UNITED STATES PATENT AND TRADEMARK OFFICE
CERTIFICATE OF CORRECTION

PATENT NO.       : 8,551,148 B2
APPLICATION NO.  : 13/069926
DATED            : October 8, 2013
INVENTOR(S)      : Asakawa et al.

Page 1 of 1

It is certified that error appears in the above-identified patent and that said Letters Patent is hereby corrected as shown below:

ON THE TITLE PAGE:

Item [75]

Replace "Seija Wada, Kanagawa (JP);" with

--Seiji Wada, Kanagawa (JP);--.

Signed and Sealed this
Third Day of June, 2014

Michelle K. Lee
*Deputy Director of the United States Patent and Trademark Office*